United States Patent [19]

Neighbors et al.

[11] Patent Number: 4,877,806

[45] Date of Patent: Oct. 31, 1989

[54] USE OF TRICYCLODECENE-3,4,7,8-TETRACARBOXYLIC ACID DERIVATIVES AS ANTI-MURINE TUMOR AGENTS

[75] Inventors: Ralph P. Neighbors, Olathe; Joseph R. Riden, Overland Park, both of Kans.

[73] Assignee: Chevron Research Company, San Francisco, Calif.

[21] Appl. No.: 170,583

[22] Filed: Mar. 18, 1988

Related U.S. Application Data

[63] Continuation of Ser. No. 504,498, Jun. 15, 1983, abandoned, which is a continuation-in-part of Ser. No. 324,882, Nov. 25, 1981, abandoned, which is a continuation-in-part of Ser. No. 231,514, Feb. 4, 1981, abandoned.

[51] Int. Cl.⁴ ............................................. A61K 31/40
[52] U.S. Cl. .................................................... 514/410
[58] Field of Search ......................................... 514/410

[56] References Cited

U.S. PATENT DOCUMENTS 4,670,461  6/1987  Haugwitz et al. .................. 514/410

OTHER PUBLICATIONS

"The Structure of the Benzene-Maleimide Photosynthetic Product (Mitindomide)", George R. Pettit, Kenneth D. Paull, Cherry L. Herald, Delbert L. Herald and Joseph R. Riden, Cancer Research Institute and Department of Chemistry, Arizona State University, pp. 2291-2294.

"Screening at the National Cancer Institute", Abraham Goldin, John M. Venditti and Stephen K. Carter, National Cancer Institute Monograph: USA-USSR.

Primary Examiner—Jerome D. Goldberg

[57] ABSTRACT

The method which comprises administering to a tumor-containing animal derivatives of tricyclodecene-3,4,7,8-tetracarboxylic acid derivatives, preferably a compound having the following structural formula:

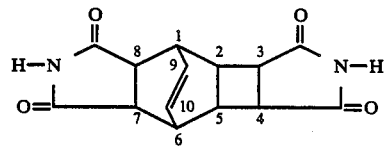

or a pharmaceutically acceptable salt thereof.

2 Claims, No Drawings

USE OF TRICYCLODECENE-3,4,7,8-TETRACARBOXYLIC ACID DERIVATIVES AS ANTI-MURINE TUMOR AGENTS

This application is a continuation of application Ser. No. 504,498, filed June 15, 1983, now abandoned, which is a continuation-in-part application of our application Ser. No. 324,882 for Use of Tricyclodecene-3,4,7,8-tetracarboxylic Acid Derivatives as Antitumor Agents, filed Nov. 25, 1981, now abandoned which, in turn, was a continuation-in-part application of our application Ser. No. 231,514 for Use of Tricyclodecene-3,4,7,8,-tetracarboxylic Acid Derivatives as Antitumor Agents, filed Feb. 4, 1981 now abandoned.

DESCRIPTION OF THE INVENTION

The preferred method of treating malignancies comprises administering to a mammal in therapeutically effective dosage a compound having the structural formula:

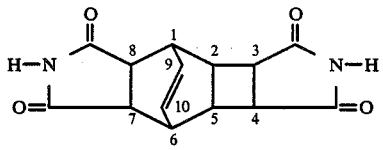

or a pharmaceutically acceptable salt thereof.

The preferred antitumor agent, the diimide of tricyclo[4.2.2.0$^{2,5}$]dec-9-ene-3,4,7,8-tetracarboxylic acid, is disclosed in U.S. Pat. No. 3,366,642 of Bradshaw. The compound is known to have utility in the polymer arts.

Synthesis of the Antitumor Agents

The synthesis of the class of antitumor agents may be illustrated by the method employed to make the preferred compound, which can be prepared by the light catalyzed reaction of maleimide with benzene in the presence of a trace quantity of a photo-initiator such as acetophenone (see U.S. Pat. No. 3,366,642).

Reaction

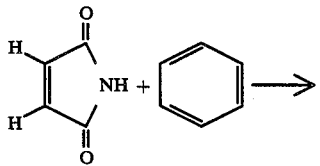

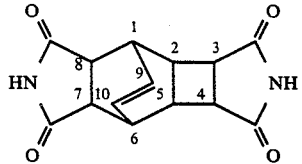

Monosubstituted benzenes produce the corresponding-9-position substituted analogs. Various other derivatives can be prepared by known reactions of the imide functional group to form salts, N-alkylated products, and/or imide ring-opening reactions. Additional derivatives can be prepared via reactions of the 9,10-position double bond.

Use of the Compounds to Treat Malignancies

The preferred compound, the diimide of tricyclo[4.2.2.0$^{2,5}$]dec-9-ene-3,4,7,8-tetracarboxylic acid and its pharmaceutically acceptable salts exhibit an inhibitory effect on the growth of several types of tumors. A suitable method of administering the compound and its salts is by subcutaneous or intraperitoneal injection. Intravenous cysis, or other methods commonly used for administering antitumor agents, for example, oral administration can also be employed. The free diimide or salt is preferably dispersed in a physiologically compatible, liquid extending medium at a low enough concentration so as to facilitate measurement and adjustment of dosage. The dispersing medium is preferably water-miscible, for convenience in dilution and use by conventional techniques.

Determination of dosage must take into account many factors such as body weight and other factors in the physical condition of the mammal, as well as the efficacy of the antitumor agent. As a measure of efficacy, there are presented below data resulting from standard screening tests by procedures of the National Cancer Institute.

A detailed description of the test procedures used by NCI may be found in an article from "Methods of Development of New Anticancer Drugs," U.S.A.—U.S.S.R. Monograph #45, National Cancer Institute, March 1977. Similar test data are available for other antitumor agents, which may be used for purposes of comparison as an aid in deciding upon dosage rate. Dependent upon the tumor test system, the NCI tests used either tumor weight inhibition or median survival time of the animals as the criteria for evaluating the compound's effectiveness:

(1) Animal Survival Time

In general, a minimal increase in survival time of the treated animals over the untreated control animals resulting in a T/C $\geq$ 125% (note 1) is necessary to justify further testing.

(2) Tumor Inhibition

In these test systems, median tumor weight inhibition of the treated animals when compared to the untreated controls (expressed as a T/C percentage-note 2) is the criterion for evaluation. In these systems, the smaller the number-the more active the compound. A negative number, not only indicates tumor growth inhibition, it indicates an actual decrease in tumor weight as a result of the treatment. A T/C value $\leq$ 42% is necessary to justify further testing.

Note 1
$$T/C = \frac{\text{Survival time of treated animals}}{\text{Survival time on untreated controls}} \times 100$$
(expressed as a %)

Note 2
$$T/C = \frac{\text{Change in tumor weight of treated animals}}{\text{Change in tumor weight of untreated controls}} \times 100$$

Test results obtained by treatment with the preferred compound in five different tumor test systems are shown in Tables I & II. Note that tumor test systems listed in Table I use survival time of the animals as the criteria for evaluation; whereas Table II lists results in which tumor weight inhibition is the criterion for measuring activity.

TABLE I

| Tumor Test System | Evaluation Criteria | Dose/Injection (mg/Kg) | T/C Value |
|---|---|---|---|
| PS31 (P388 Lymphocytic Leukemia) | Survival Time | 100 | 176[1] |
| LE21 (L—1210 Lymphoid Leukemia) | Survival Time | 50 | 188[1] |
| B131 (B16 Melanocarcinonoma) | Survival Time | 50 | 139[1] |

[1] The T/C values of 176, 188 and 139 indicate that the treated animals lived 76, 88 and 39% longer than the untreated control animals.

TABLE II

| Tumor Test System | Evaluation Criteria | Dose/Injection (mg/Kg) | T/C Value |
|---|---|---|---|
| C 872 (Colon 38) | Median Tumor Weight | 200 | 22,29(2 tests) |
| CDJ2 (Mammary Tumor) | Median Tumor Weight | 250 | −25, −19(2 tests)[1] |

[1] A negative number such as that obtained when test animals were treated with the preferred compound in the mammary tumor test system indicates that the tumor actually decreased in weight (25% and 19%) from the first treatment date until evaluation day. In these instances, the T/C value is calculated as follows:

$$T/C = \frac{\text{Change in tumor weight of treated animals}}{\text{Initial tumor weight of treated animals}} \times 100$$

Additional runs have been made wherein a non-toxic formulation of the diimide of tricyclo[4.2.2.0$^{2,5}$]dec-9-ene-3,4,7,8-tricarboxylic acid as a solution in sodium hydroxide with added mannitol, amounting to 50 mg/kg/day, was administered intravenously for nine days in mice with implanted L1210 lymphoid leukemia, resulting in an increased life span of 76 percent. A similar pattern of effectiveness was observed following oral dosages of 800 mg/kg/day.

Obviously, many modifications and variations of the invention, as hereinabove set forth, can be made without departing from the spirit and scope thereof, and therefore only such limitations should be imposed as are indicated in the appended claims.

We claim:

1. A method of treating mammals afflicted with murine tumors comprising administering to said mammals in a therapeutically effective amount sufficient to increase survival time or inhibit tumor growth the diimide of tricyclo[4.2.2.0$^{2,5}$]dec-9-ene-3,4,7,8-tetracarboxylic acid or a pharmaceutically acceptable salt thereof.

2. A therapeutic composition for treating murine tumors comprising a therapeutically effective amount sufficient to increase survival time or inhibit tumor growth of the diimide of tricyclo[4.2.2.0$^{2,5}$]dec-9-ene-3,4,7,8-tetracarboxylic acid, or a pharmaceutically acceptable salt thereof, as an active ingredient and a pharmaceutically acceptable additive or carrier.

* * * * *